(12) United States Patent
Hilfiker

(10) Patent No.: US 7,794,138 B2
(45) Date of Patent: Sep. 14, 2010

(54) DEVICE FOR OPERATING AN ELECTRONIC MULTIFUNCTIONAL DEVICE

(76) Inventor: Beppo Hilfiker, Mohrhaldenstrasse 185, CH-4125 Riehen (CH)

( * ) Notice: Subject to any disclaimer, the term of this patent is extended or adjusted under 35 U.S.C. 154(b) by 0 days.

(21) Appl. No.: 12/316,919

(22) Filed: Dec. 16, 2008

(65) Prior Publication Data
US 2009/0175130 A1 Jul. 9, 2009

(30) Foreign Application Priority Data
Dec. 19, 2007 (CH) ..................... 1974/07

(51) Int. Cl.
*G04B 29/00* (2006.01)
(52) U.S. Cl. .................. 368/190; 368/308; 368/319
(58) Field of Classification Search ............. 368/308, 368/319, 146, 190–199, 216, 288–290, 306–307
See application file for complete search history.

(56) References Cited

U.S. PATENT DOCUMENTS

| | | | | |
|---|---|---|---|---|
| 1,619,877 A | * | 3/1927 | Melhinch | 200/35 A |
| 1,913,849 A | * | 6/1933 | Neureuther | 368/64 |
| 1,990,012 A | * | 2/1935 | Woodruff | 368/22 |
| 2,241,447 A | * | 5/1941 | Demonet | 368/191 |
| 3,638,418 A | * | 2/1972 | Spadini | 368/74 |
| 3,992,949 A | * | 11/1976 | Edmondson | 73/865.1 |
| 4,035,617 A | * | 7/1977 | Banner | 235/88 N |
| 4,444,511 A | * | 4/1984 | Ogihara et al. | 368/69 |
| 4,740,936 A | * | 4/1988 | Tanaka | 368/319 |
| 5,305,291 A | * | 4/1994 | Kamens et al. | 368/252 |
| 5,644,553 A | * | 7/1997 | Cuinet | 368/320 |
| 7,120,093 B2 | * | 10/2006 | Lazaretnik | 368/80 |
| 7,272,077 B2 | * | 9/2007 | Nobs | 368/69 |
| 2008/0089185 A1 | * | 4/2008 | Martin et al. | 368/282 |

* cited by examiner

*Primary Examiner*—Vit W Miska
*Assistant Examiner*—Sean Kayes
(74) *Attorney, Agent, or Firm*—Pauley Petersen & Erickson

(57) ABSTRACT

An operating mechanism of a multifunctional device which can be worn on the wrist and has a housing with integrated electronics. The operating mechanism is integrated into the housing and has an operating element which is a one-piece or multi-piece setting stem. The setting stem partly crosses the housing, and the setting stem is arranged parallel to a planar enlargement of the housing and is rotatably and linearly moveably mounted. The setting stem can be moved linearly parallel to the longitudinal axis and rotatively about the rotational axis/longitudinal axis by a first operating watch button and optionally with a second operating watch button. The movement of the setting stem triggers various contacts on a contact plate, from which contacts electronic signals are sent to the electronics, as a result of which the electronic control of the multifunctional device is effected.

12 Claims, 5 Drawing Sheets

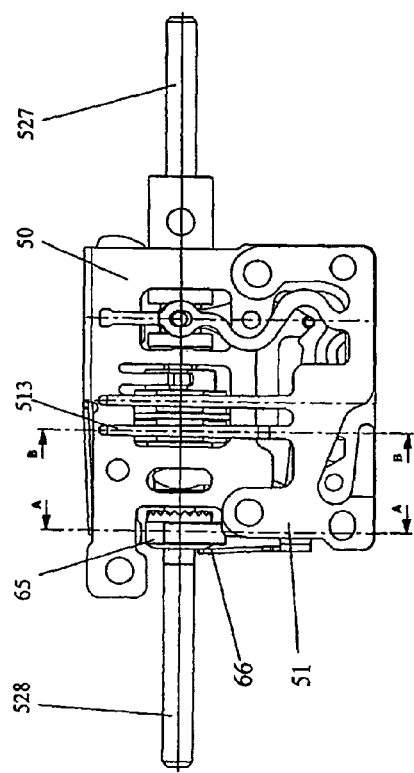
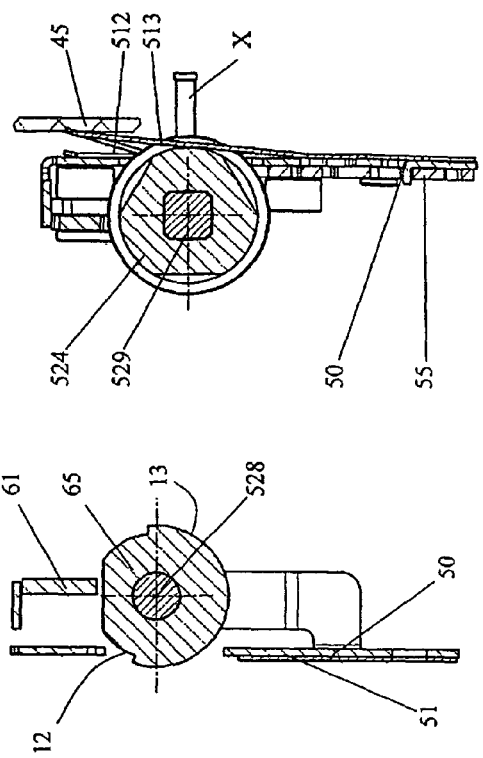
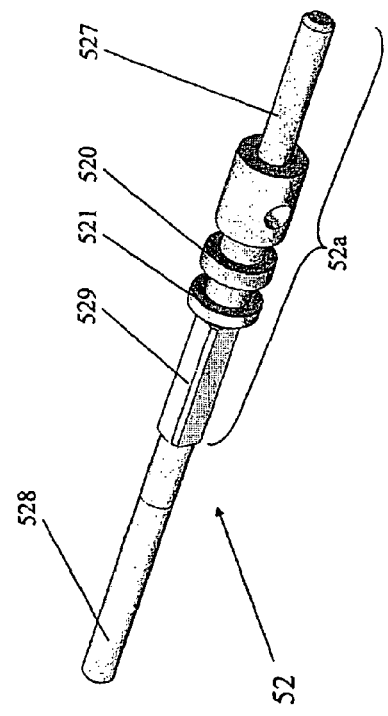
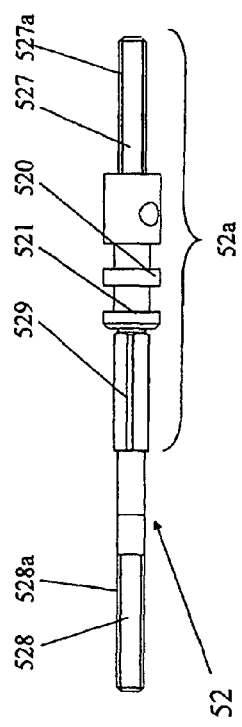

DEVICE FOR OPERATING AN ELECTRONIC MULTIFUNCTIONAL DEVICE

BACKGROUND OF THE INVENTION

1. Field of the Invention

This invention relates to an operating mechanism of an electronic multifunctional device which can be worn on the wrist of a person, particularly a pulse monitor, a playback device for multimedia applications or a communication device, wherein the multifunctional device has a housing with a housing edge which is releasably fastened to the wrist by a wrist strap, and within the housing, the operating mechanism and integrated electronics, which can be controlled by a plurality of electronic contacts and which includes at least one multi-celled display unit and a sensor unit with a plurality of sensors for various measurements, are arranged, wherein at least one microprocessor controls data processing, the display of values on the display unit and the saving of values.

2. Discussion of Related Art

In recent years, a multiplicity of electronic multifunctional devices which can be fastened and worn portably on the wrist of a person have come onto the market. Mobile multifunctional devices such as for example multimedia players, pulse monitors, mobile telephones and navigation devices, are used, in addition to the measurement of physiological parameters, for entertainment and communication or as navigation aids and have become indispensable in modern life.

The design of these electronic multifunctional devices includes a housing into the interior of which electronics, which control the multifunctional device with one or a plurality of processors, are placed. With electronics, data is measured, captured, evaluated and displayed on a display unit which is integrated into the housing and can mostly be saved on a hard disk. In the past, a plurality of operating elements in the form of operating keys were used to control the multifunctional devices, which are becoming more and more complex all the time, and which keys can be pressed into the housing and the number of which rose to five and more operating keys. Now, a result of which a multiplicity of setting possibilities can be made.

As the actual multifunctional devices often already have widely branched menu trees which can be read on a display unit and through which the user can navigate, however, simple operating keys have reached their limit.

In multimedia players, navigating through a main menu and submenus subordinated to this is provided by operating buttons. While a first operating button is provided to navigate up and down within a menu, a second operating button is required to access a submenu. In order to access the next highest menu, a third operating button is used or a key combination of the first and second buttons must be pressed at the same time, which leads to a more difficult setting for the user.

In addition to the classic operating buttons which are pushed some distance into the housing of the multifunctional device, to some extent settings dials, which are rotatably mounted in the housing are also used, which settings dials can be rotated about a rotational axis using the tip of a finger and by moving which settings dials, the user can navigate up and down in a menu. Levers, which are mounted pivotably about a lever axis located in the housing, are also used in order to be able to carry out what is known as "scrolling" through menus and submenus.

The number of the operating keys increased during development and the type of operating keys are varied. Now, touch sensitive membrane keys can be found in some devices, whereby scrolling is realized by gliding a finger over a plurality of membrane keys in short time intervals. In spite of this, a plurality of operating elements is required in order to provide a plurality of settings possibilities.

Devices of the prior art have a plurality of operating elements with different embodiments in order to realize scrolling in a menu structure, whereby a minimal number of operating keys, settings dials or levers is required. The combination of a dial or lever which can be pressed into and is moveably mounted in the housing is also known, as a result of which scrolling is achieved by rotating/pivoting the settings dial/lever, while accessing a submenu can be accomplished by pressing in the settings dial/lever.

If, starting from a main menu, a deeper submenu is scrolled through, pressing the settings dial/lever into the housing can be provided, and following pressing a next-deepest submenu is accessed. Pressing for a longer period, which is detected by the electronics, is mostly provided for returning to the next-highest submenu, so that repeated longer-lasting pressing actions allow scrolling back to the highest menu. The settings possibilities are limited for known settings possibilities of a rotatably moveable settings dial or lever and the user desires alternatives.

As portable electronic multifunctional devices should be as small, light and handy as possible, only a small number of operating elements can be applied to the housing, whereby the size of the operating keys must be adapted to the size of a finger tip of a user. The previously known electronic multifunctional devices are still difficult for users with larger hands and fingers to use and for actuation when wearing gloves is often impossible.

SUMMARY OF THE INVENTION

This invention has one object of providing a device for operating a watch-like electronic multifunctional device with a multi-celled display unit, which multifunctional device can be worn on the wrist and can be used to navigate through a menu structure of the multifunctional device, whereby the user is only required to actuate a single operating element. By actuating the one operating element, it is possible to scroll in one menu, change the menu to widely branched submenus and return to the main menu, simply and conveniently.

These objects and the operation of the multifunctional device while avoiding the simultaneous pressing of a plurality of keys or the following actuation of key combinations is achieved by this invention.

In one embodiment, an operating mechanism according to this invention is used for multifunctional devices in the field of sport, for example for pulse monitors and sports watches. It is another object of this invention to provide and facilitate the operability for users with hands wet from sweat and users with sports gloves or with winter gloves in the case of cold weather, so that settings can be made simply and conveniently during the practice of the sport, and the hands are not required to be dried and gloves are not required to be removed.

BRIEF DESCRIPTION OF THE DRAWINGS

One operating mechanism according to this invention of an electronic multifunctional device which can be worn on the wrist of a person is described in view of the drawings, which show one possible embodiment, wherein:

FIG. 9a shows a view of the contact plate according to FIG. 8a;

FIG. 10a shows a perspective view of one embodiment of the setting stem;

FIG. 10b shows a two-dimensional view of the setting stem of FIG. 10a, whereby external threads are marked;

FIG. 11 shows a view of the contact plate of a possible operating mechanism;

FIG. 11a shows a section corresponding to the section line A-A of FIG. 11; and

FIG. 11b shows a section corresponding to the section line B-B of FIG. 11.

DETAILED DESCRIPTION OF THE INVENTION

Figure 1:
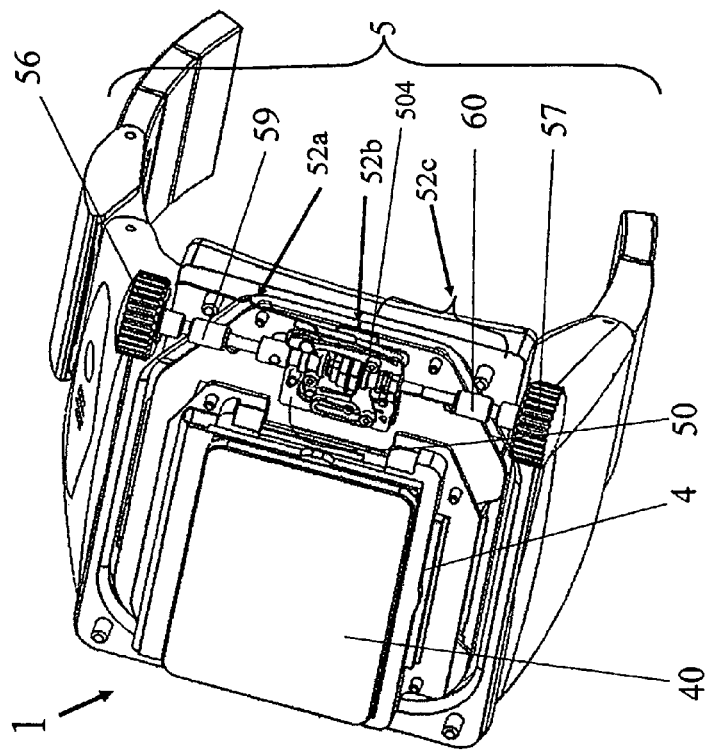
FIG. 1 shows a perspective view of a multifunctional device according to one embodiment of this invention, with a setting stem in the neutral position.

An operating mechanism 5 according to this invention of an electronic multifunctional device 1 can be worn on the wrist of a person and is described using one example of a pulse monitor 1. In addition to pulse monitors, multimedia playback devices as well as communication devices and further measuring devices can be equipped with the operating mechanism of this invention.

A possible embodiment of a pulse monitor 1 with the operating mechanism 5 according to this invention for determining parameters such as pulse, step count, air pressure, acceleration and points on the compass, comprises a housing 2 with a housing edge 20 which is fastened to a wrist strap 3 and has a multi-celled display unit 40. The above parameters can be shown in various modes on the display unit 40. A user can choose between various forms of representation on the display unit 40.

Electronics 4 are integrated within the housing 2, and the electronics 2 are connected to the operating mechanism 5 and are controlled by at least one first microprocessor 42 in a computer unit, whereby data can be measured, evaluated, saved in a memory and/or displayed. In addition to measured values, such as for example pulse rate and air pressure, which can be detected by sensors in a sensor unit 41 and can be read out by the computer unit, the computer unit accepts electronic control signals from the operating mechanism 5 which is described in detail below and processes the signals further and displays them.

The sensor unit 41 can comprise temperature sensors T, pressure sensors P, position sensors A, magnetic field sensors M, proximity sensors, which measure the proximity to the skin for example, touch sensors and UV sensors UV for example, and have means for wireless communication with other electronic devices, whereby an RF antenna is used.

Depending on the embodiment of the electronics, a second microprocessor 44 can also be integrated with the first microprocessor 42 into the electronics 4 via an interface 43, which leads to manifold possibilities.

The operating mechanism 5 is integrated into the housing 2, effectively connected to the electronics 4 and a one-piece setting stem 52 is provided as operating element, by which the various settings of the pulse monitor 1 can be made.

Figure 2:
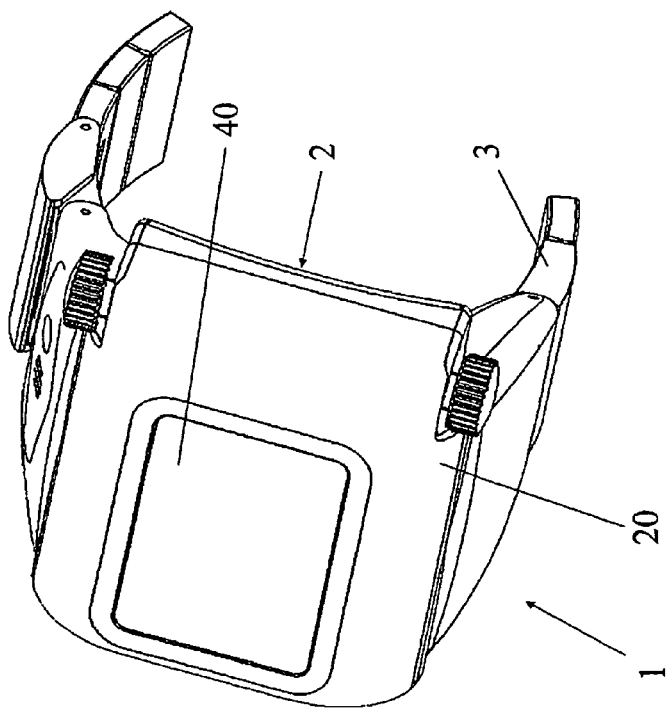
FIG. 2 shows a perspective view of the multifunctional device without a housing cover and with an exposed display unit and operating mechanism.

In a first embodiment, the setting stem 52 partly crosses the housing 2, whereby the setting stem 52 is arranged parallel to a planar enlargement of the housing 2, is rotatably and linearly moveably mounted and exits the housing 2 through a recess in the housing edge 20. The setting stem 52 should be arranged in a plane parallel to the plane in which the display unit 40 lies and could thus also be arranged or rotated by 90° relative to the orientation shown in FIG. 2, or the housing 2 can even be crossed diagonally by the setting stem 52.

Outside the housing 2, the setting stem 52 has a first operating watch button 56 which is non-positively and/or positively couplably connected to the setting stem 52 and has a corrugation along the curved surface of the operating watch button 56, as a result of which the first operating watch button 56 can be operated handily and well. The mounting of the setting stem 52 takes place in at least one first bearing 59, so that the setting stem 52 protrudes over a baseplate 50 of the operating mechanism 5 which is unreleasably fixed in the housing, whereby the setting stem 52 is mounted so that a linear displacement parallel to the longitudinal axis and a rotative movement about the rotational axis/longitudinal axis of the setting stem 52 is possible.

The setting stem 52 is described in detail and is shown in FIGS. 10a and 10b. The setting stem 52 has a first watch button pin 527 with a thread 527a at the start of the setting stem 52 and a second watch button pin 528 with a thread 528a at the end of the setting stem 52. The first watch button pin 527 is releasably connected to the first operating watch button 56 and projects out of the housing 2 of the multifunctional device 1. A first disc 520 adjoins the first watch button pin 527 and a second disc 521 adjoins the first. The first disc 520 and the second disc 521 are used for detecting the linear movement of the setting stem 52 which is described in more detail below. A web 529, which is not cylindrically shaped and which co-operates in an effectively connected manner with a counter-contact part 52b which is explained in more detail hereinbelow, is located approximately centrally in the setting stem 52.

The first watch button pin 527, the web 529, the first disc 520 and the second disc 521 are designated as shaft part 52a in the following specification. The first operating watch button 56 is positively or non-positively releasably fixed on the first watch button pin 527 of the shaft part 52a. The part of the setting stem 52 which is opposite the shaft part 52a is designated the coupling part 52c in the following and, in addition to the second watch button pin 528 with thread 528a, comprises a coupling drive 525 with a first cogwheel 525a as well as a profile disc 65 with a second cogwheel 64. While the coupling drive 525 is connected, by the first cogwheel formed thereon or fixed thereto, to the setting stem 52 such that it moves with it, the profile disc 65 is connected, by the second cogwheel 64 formed thereon or fixed thereto, to the operating mechanism 5 so that it cannot move.

The counter-contact part 52b is mounted rotatively moveably and linearly immovably on the base plate 50 of the operating mechanism 5. The counter-contact part 52b comprises a first rotational-direction disc 523 and a second rotational-direction disc 524 which have holes with a rectangular cross section in each case. The setting stem 52 is rotatively and linearly moveably mounted on the base plate 50 so that the web 529 of the setting stem 52 comes to lie in the first and second rotational-direction discs 524, 525 within the hole. The second watch button pin 528 projects out of the counter-contact part 52b on the side opposite the shaft part 52a. The setting stem 52 is effectively connected to the counter-contact part 52b which is independent of the setting stem.

The rotation and the linear movement of the moveably mounted setting stem 52 can trigger various contacts on a contact plate 51 of the operating mechanism 5, from which contacts electronic signals are sent to the electronics 4, as a result of which the electronic control of the multifunctional device 1 is effected.

Figure 3:
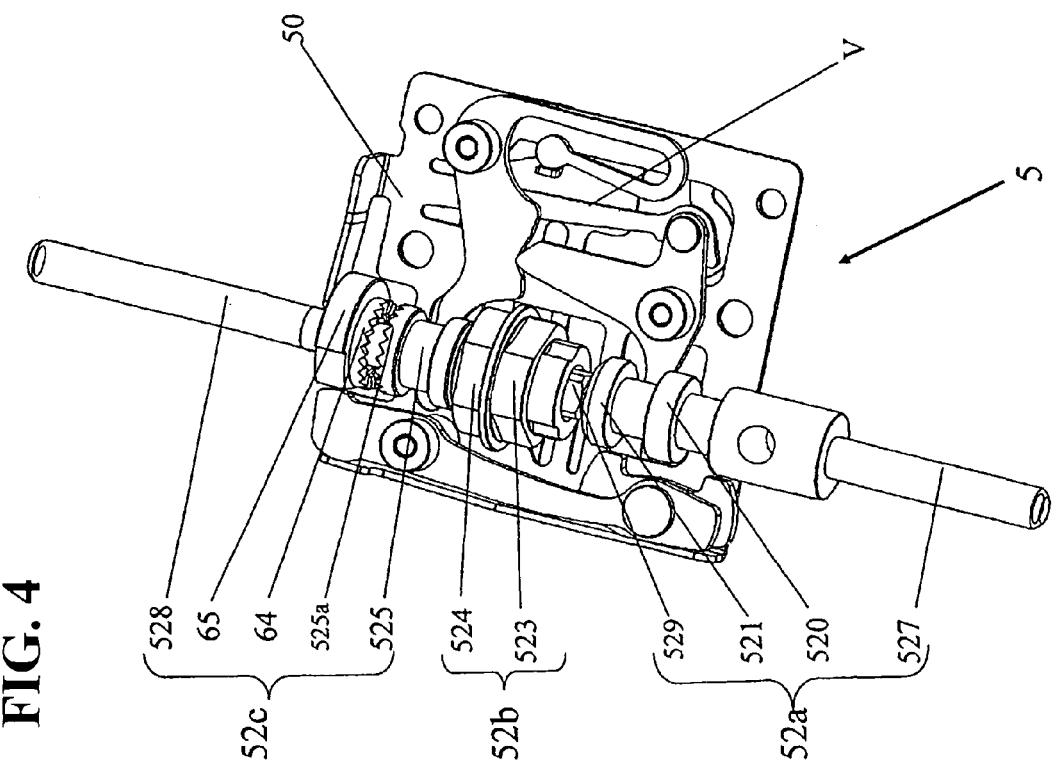
FIG. 3 shows a perspective view of the operating mechanism from a contact plate side in the neutral position of the setting stem.
Figure 4:
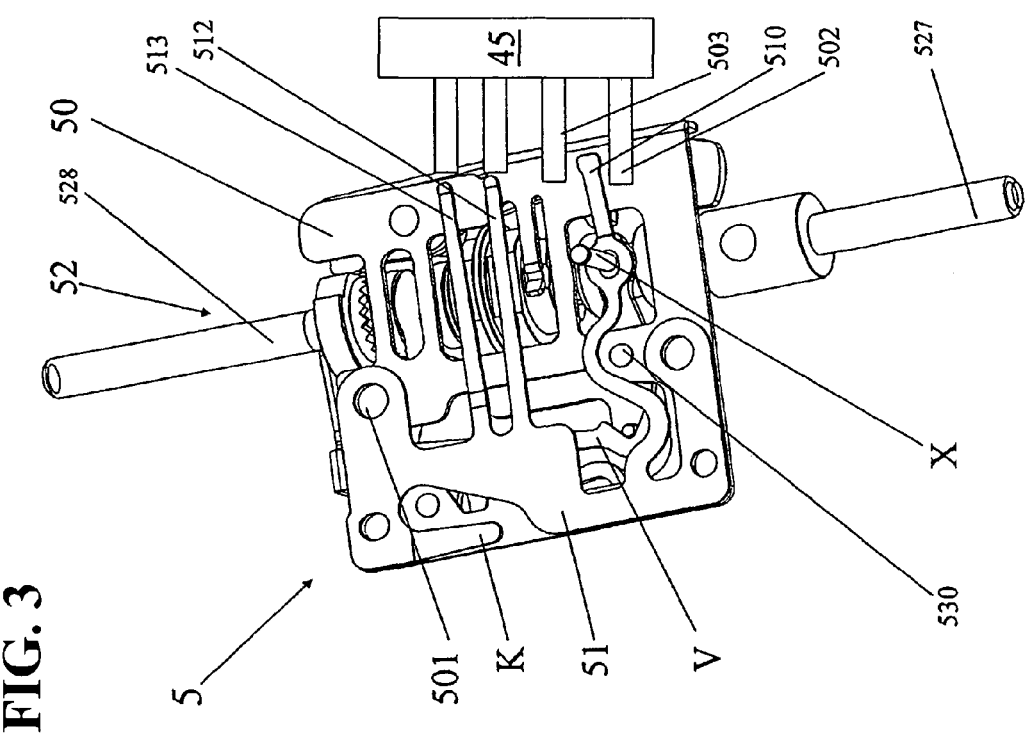
FIG. 4 shows a perspective view of the operating mechanism from a base plate in the neutral position of the setting stem.
Figure 7:
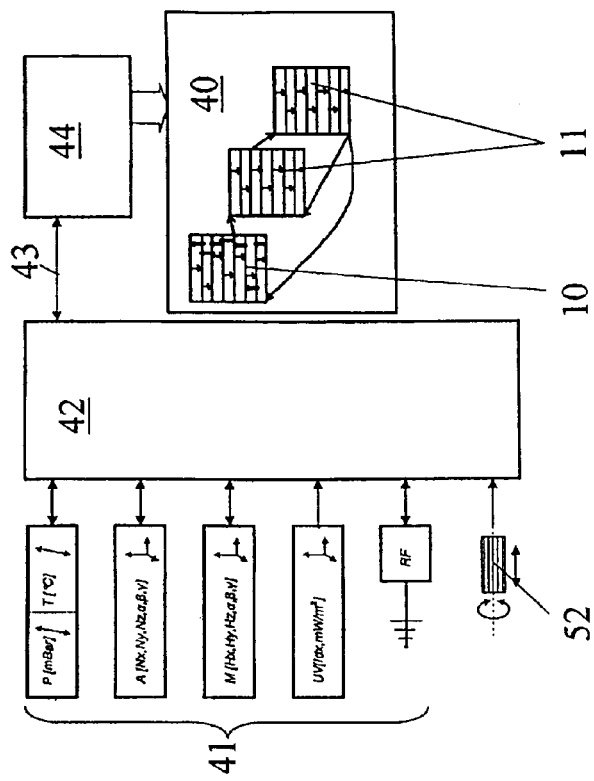
FIG. 7 shows a schematic representation of electronics with a display unit, a sensor unit and a microprocessor.
Figure 5:
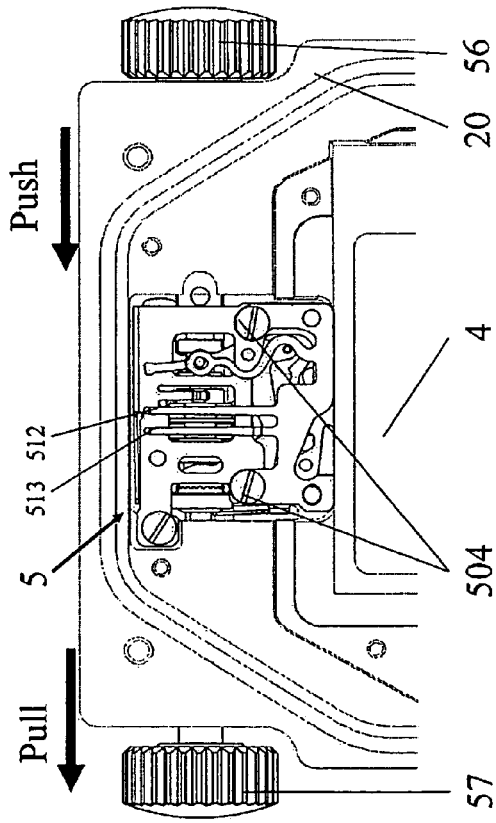
FIG. 5 shows a plan view of the operating mechanism in the push position of the first operating watch button.
Figure 6:
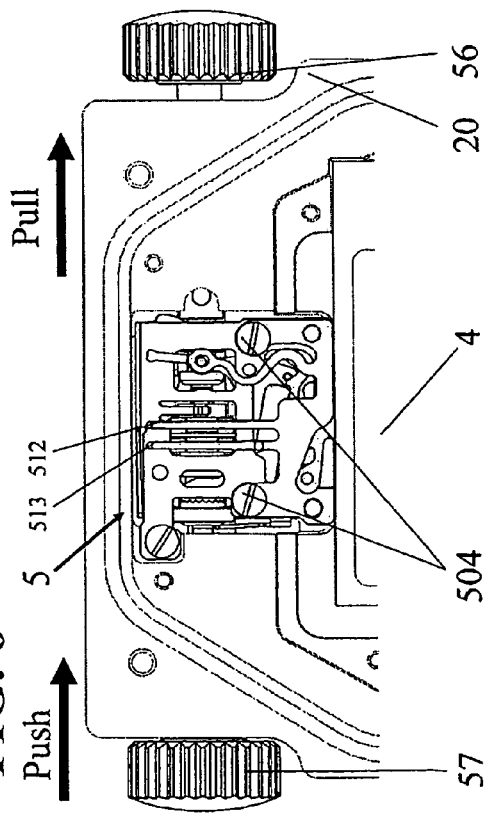
FIG. 6 shows a plan view of the operating mechanism with two operating watch buttons in the pull position of the first operating watch button.

The base plate 50 and the contact plate 51 have at least one drilled hole 501 and are unreleasably fixed in the housing 2 with fixing means 504. A circuit board 45 is schematically indicated in FIG. 3, which circuit board forwards electrical signals to the electronics 4 and is arranged to be electrically insulated from the base plate 50. A contact stud K of the contact plate 51 is always electrically conductively connected to the circuit board 45. A front linear contact 502 and a rear linear contact 503 are triggered as a function of the direction of a linear displacement of the setting stem 52. The linear displacement of the setting stem 52 leads to a deflection of a setting lever 53 which is pivoted about a setting lever axis 530, whereby a setting lever spring V is tensioned. A setting lever pin X which is connected to the setting lever 53 deflects a linear movement contact 510 on the contact plate 51, which in turn makes contact with the front or the rear linear contact 502, 503. The linear contacts 502, 503 are thereby triggered by the linear movement of the setting stem 52 as a function of the movement direction, as a result of which corresponding signals for characterizing the movement direction are forwarded to the electronics 4.

If the shaft part 52a of the setting stem 52 is pressed in the direction of the longitudinal axis and the rotational axis of the setting stem 52, then the linear movement contact 510 between the first disc 520 and the second disc 521 of the shaft part 52a is pushed in a horizontal position against the rear linear contact 503 and is known as a "Push" signal which is sent to the electronics 4, while the setting stem 52 is in the push position. If the shaft part 52a of the setting stem 52 is pulled, then the linear movement contact 510 touches the front linear contact 502 and what is known as a "Pull" signal is sent to the electronics 4, while the setting stem 52 is in the pull position.

In a further embodiment, the electronics 4 can be programmed so that a long-push or a long-pull signal is assigned to a push signal or a pull signal over a longer period of time, which leads to a further manipulation parameter, using which settings of the multifunction device 1 can be made. So if the setting stem 52 is held pressed or pulled for a time period of several hundred milliseconds, then the electronics 4 recognizes this as a long-push or long-pull signal.

In one possible embodiment, the operating mechanism 5 according to this invention has the first rotational-direction contact 512 and the second rotational-direction contact 513, which are of tongue-shaped configuration, on the contact plate 51 to detect the rotational movement and rotational direction. The first rotational-direction disc 523 and the second rotational-direction disc 524 on the counter-contact part 52b co-operate with the first and second rotational-direction contacts 512, 513. Both rotational-direction discs 523, 524 are shaped identically and each have flat planar surface sections and convex surface sections equivalent to a curved control disc alternately along the outer disc circumference. As a result of the rotation of the setting stem 52, the rotational-direction discs 523, 524 correspondingly press the rotational-direction contacts 512, 513 upwards against the circuit board 45, as a result of which electrical signals are sent to the electronics 4. In addition to the generating of electrical signals by the mechanical turning of the rotational-direction discs 523, 524, other trigger mechanisms of electrical signals in the electronics 4 are also possible.

As the first rotational-direction disc 523 is fixed on the counter-contact part 52b in such a manner relative to the second rotational-direction disc 524, where in each case only one rotational-direction contact 512, 513 is in electrical contact with the corresponding rotational-direction disc at one time, the electronics 4 can detect the rotational direction of the setting stem 52, so that the physical movement of the setting stem 52 can be used to move through menus 10 and submenus 11 on the display unit 40. Depending on the direction of rotation of the setting stem 52, an upwards scrolling or downwards scrolling in menus and submenus by the user is thus enabled.

The setting stem 52 of this invention has a counter-contact part 52b, which is configured to be rotatively moveable but linearly immovable relatively to the base plate 50 and the contact plate 51, so that the electrical contacts 512, 513 can reach the corresponding rotational-direction discs 523, 524 at all times. Thus, the counter-contact part 52b is always in contact with at least one first rotational-direction contact 512, as well as with at least one second rotational-direction contact 513. The linear immovability can be achieved with a counter-contact-part bearing which prevents movement relative to the operating mechanism 5.

As soon as the setting stem 52 is pressed by the first operating watch button 56 and, as a result, a push signal or a long-push signal is executed and detected by the electronics 4, the multifunctional device 1 can be controlled. Likewise, a pull signal or a long-pull signal can be used to manipulate the multifunctional device 1. The first embodiment of a multifunctional device 1 of this invention comprises an operating mechanism 5 with only one operating element, a setting stem 52, by which a push and a long-push signal, a pull and a long-pull signal and two scroll signals can be forwarded to the electronics 4, and thus the setting stem 52 can be moved from a neutral position into a push position and into a pull position.

A provided resilience of the setting stem 52 which acts by the resilience of the setting lever spring V against the setting lever 53 or can be achieved by the resilient tongue-shaped configuration of the linear movement contact 510, leads to the setting stem 52 moving back to the neutral position following the linear deflection in the event of the absence of push or pull, so that a menu 10 can be scrolled through and various parameters can be set by the rotation of the setting stem 52. The rotation of the setting stem occurs during the operation of the multifunctional device 1 without linear push or pull, so that only the rotational-direction contacts 512, 513 are then activated in the case of the rotation of the setting stem 52.

As a result of a correspondingly large configuration of the first operating watch button 56, a user can also use the setting stem 52 of the operating mechanism 5 and set a desired display with hands wet from sweat or with gloves on their hands.

In a further embodiment of the operating mechanism 5, the setting stem 52 is passed, crossing the housing 2 completely and thus in an active manner continuously through the housing 2, whereby the second watch button pin 528 exits the housing 2. A second operating watch button 57 is non-positively and/or positively fixed onto the second watch button pin 528 which emerges from the housing 2, which operating watch button has, like the first operating watch button 56, means which improve the roughening or frictional grip, such as a corrugation, as a result of which the gripability is increased and the user-friendliness is increased. The setting stem 52 which crosses the housing 2 completely is rotatively and linearly moveably held in a second bearing 60, as a result of which a greater stability is achieved.

The movement of the setting stem 52 can in this embodiment optionally be configured with the first or the second operating watch button 56, 57, whereby the push position of the setting stem 52 can be achieved by a linear push movement of the first operating watch button 56 in the direction of the housing 2 or a pull movement of the second operating watch button 57 away from the housing 2, which in each case leads to a push signal or a long-push signal to the electronics 4. It behaves correspondingly with the pull position and thus the generation of a pull signal or a long-pull signal.

By possibly operating the setting stem 52 from two diametrically opposed sides of the housing 2, the operating mechanism 5 of this invention can be operated equally well by left-handed people and right-handed people.

Figure 8A:
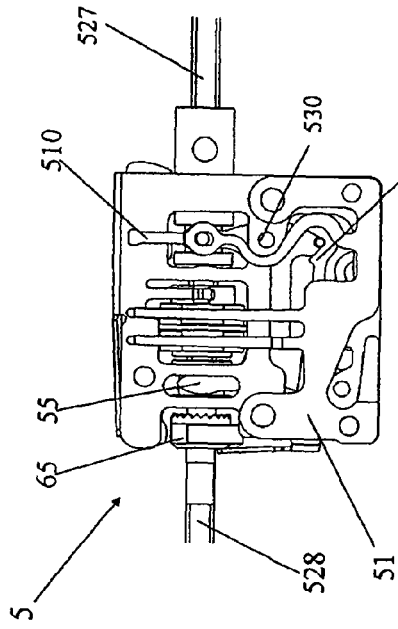
FIG. 8a shows a view of the base plate, with the setting stem in the neutral position.
Figure 8B:
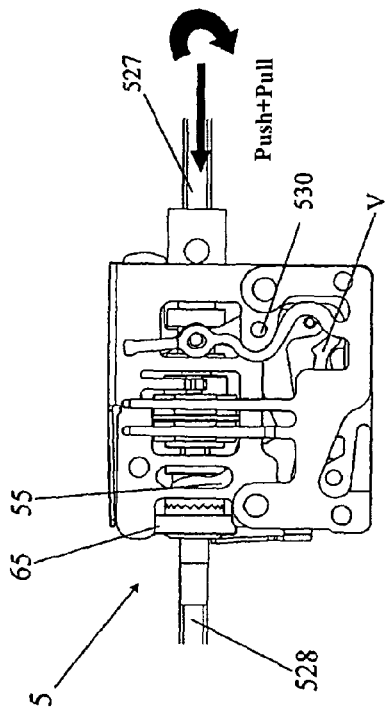
FIG. 8b shows a view of the base plate, with the setting stem in the stop position.
Figure 9A:
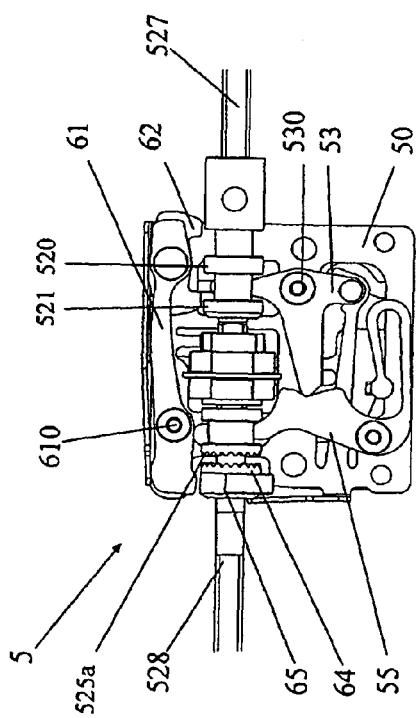
Figure 9B:
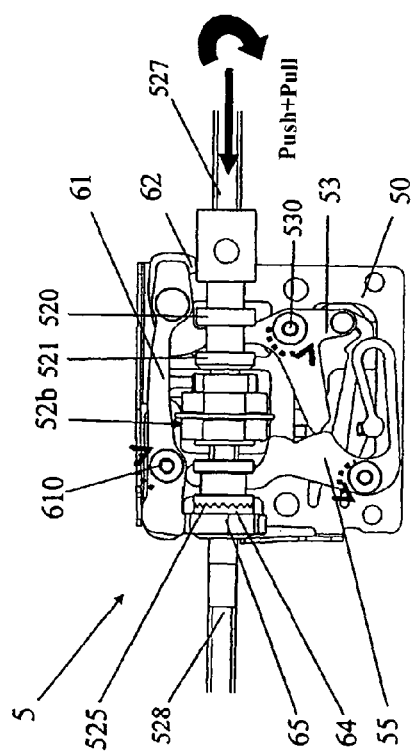
FIG. 9b shows a view of the contact plate according to FIG. 8b with the setting stem in the stop position.

The operating mechanism 5 according to this invention has a stop mechanism which can be used independently of whether the operating mechanism has only a first operating watch button 56 or a first operating watch button 56 and a second operating watch button 57. This stop mechanism is used to prevent an undesirable actuation of the setting stem 52. One possible embodiment of a stop mechanism is shown in FIGS. 8a and 8b, where FIG. 8a shows a view of the operating mechanism 5 onto the base plate 50, and the setting stem 52 is in the undeflected neutral position in which no deflection of the linear movement contact 510 is present.

In order to secure the electronic multifunctional device 1 against actuation of the setting stem 52 and thus against an undesirable input of signals, the coupling part 52c is provided in the region downstream of or near the web 529 after passing through the counter-contact part 52. The coupling drive 525, comprising the first cogwheel 525a is placed onto the web 529 with a rectangular cross section in such a manner that it can be moved with the setting stem 52. The coupling drive 525 also performs the linear displacement and the rotational movements of the setting stem 52, as the web 529 correspondingly entrains the coupling drive 525. The second watch button pin 528 with circular cross section projects through a hole in the profile disc 65 which likewise has a circular cross section. The profile disc 65 is linearly immovably mounted on the base plate 50 by a disc bearing 66 so that the second watch button pin 528 can pass in and out through the profile disc 65.

The second cogwheel 64 formed on the profile disc 65 accommodates the first cogwheel 525a when the setting stem 52 is pushed in the direction of the housing 2 by the operating watch button 56, and a push movement is carried out, or when the setting stem 52 is pulled out of the housing 2 with the second operating watch button 57, a pull movement is carried out.

In the embodiment of a stop mechanism described here, a setting lever 53, a stop rocker 55 and a locking lever 61, which are fixed to the base plate 50 so as to be co-operatively pivotable, are provided. When the setting stem 52 is pressed, the setting lever 53 is pivoted about a setting lever axis 530. The side of the stop rocker 55 which faces the setting stem 52 is guided in the direction of the push movement by the setting lever 53, and as a result a spring tension is created in the direction opposite to the push movement. The first cogwheel 525a engages into the second cogwheel 64 of the profile disc 65 in this process.

If a rotation of the setting stem 52 is carried out during the push movement, then the profile disc 65 is rotated, as the first cogwheel 525a engages into the second cogwheel 64. In the case of the rotation of the profile discs 65, the outer circumference of the profile disc 65 deflects the pivotably moveably mounted locking lever 61, so that the locking lever 61 is pivoted about a locking lever axis 610 in the direction of the setting stem 52.

A lever bolt 62, which is pivotably fixed on the locking lever 61, engages between the first disc 520 and the second disc 521, as a result of which the linear displacement of the setting stem 52 is prevented and no further push or pull signals can be sent. The signals arising in the event of the further rotation of the setting stem 52 are not processed by the electronics 4, as the push signal is triggered simultaneously.

In the embodiment selected here, the profile disc 65 has a profiling which comprises a small circle sector with a small arc and a large circle sector with a large arc. This is shown in detail in FIG. 11a. The outer circumference of the profile disc 65 only actuates the locking lever 61 when the large arc rests against the locking lever 61. If the setting stem 52 is turned back or turned further so that the small arc is opposite the locking lever 61, then the profile disc 65 is no longer in contact with the locking lever 61, and thus stopping the setting stem 52 is ended by pivoting the locking lever 61 back. The rotational movement can take place clockwise or anti-clockwise to stop the setting stem 52. The type of stop mechanism described here allows rotation in both possible directions.

In one embodiment, a configuration of the operating mechanism 5 has a first operating watch button 56 and a second operating watch button 57. Actuation of the stop mechanism with the first operating watch button 56 or the second operating watch button 57 is provided and results in the push movement of the first operating watch button 56 corresponding to the pull movement of the second operating watch button 57.

The engagement of the first cogwheel 525a into the second cogwheel 64 is possible at every angular position of the setting stem 52 so that the stopping can be carried out at any time by pressing the setting stem 52 into the housing or by the corresponding pull movement of the setting stem 52 with the second operating watch button 57 while at the same time turning the setting stem 52. This possibility of stopping is significantly simpler and more user friendly than the stopping mechanism of wristwatches.

Stopping the setting stem 52 is also possible by pulling the second watch button pin 528 out of the housing 2, which corresponds to the pressing of the shaft part 52a into the housing. As the setting stem 52 is mounted in a suspended manner above the operating mechanism 5, it is possible to stop the setting stem 52 by pressing the coupling part 52c into the housing 2, whereby the second cogwheel 64 engages into the first cogwheel 525a and the stopping can be executed as described above.

Swiss Patent Reference 01974/07, filed on 19 Dec. 2007, the priority document corresponding to this invention, and its teachings in entirety are incorporated, by reference, into this specification.

The following is a list of reference numerals and the corresponding element.

| | |
|---|---|
| 1 | Electronic multifunctional device |
| 2 | Housing |
| 20 | Housing edge |
| 3 | Wrist band |
| 4 | Electronics |
| 40 | Display unit |

-continued

| | |
|---|---|
| 41 | Sensor unit (pressure sensor, position sensor, magnetic field sensor, UV Sensor, RF interface with antenna) |
| 42 | First microprocessor |
| 43 | Interface |
| 44 | Second optional microprocessor |
| 45 | Circuit board |
| 5 | Operating mechanism |
| 50 | Base plate |
| 501 | Holes for fixing the base plate in/to the housing |
| 502 | Front linear contact |
| 503 | Rear linear contact |
| 504 | Fixing means |
| 51 | Contact plate |
| 510 | Linear movement contact |
| 512 | First rotational-direction contact |
| 513 | Second rotational-direction contact |
| 52 | Setting stem (operating element) |
| 52a | Shaft part |
| 520 | First disc |
| 521 | Second disc |
| 527 | First watch button pin |
| 527a | Thread |
| 528 | Second watch button pin |
| 528a | Thread |
| 529 | Web |
| 52b | Counter-contact part |
| 523 | First rotational-direction disc |
| 524 | Second rotational-direction disc |
| 52c | Coupling part |
| 525 | Coupling drive |
| 525a | First cogwheel |
| 53 | Setting lever |
| 530 | Setting lever axis |
| 55 | Stop rocker |
| 56 | First operating watch button |
| 57 | Second operating watch button |
| 59 | First bearing |
| 60 | Second bearing |
| 61 | Locking lever |
| 610 | Locking lever axis |
| 62 | Lever bolt |
| 64 | Second cogwheel |
| 65 | Profile disc |
| V | Setting lever spring |
| X | Setting lever pin |
| K | Contact stud |
| 10 | Menu |
| 11 | Submenu |
| 12 | Small arc |
| 13 | Large arc |

What is claimed is:

1. An operating mechanism of an electronic multifunctional device which is attachable to a wrist of a person, including a pulse monitor, a playback device for multimedia applications or a communication device, wherein the multifunctional device has a housing with a housing edge releasably fastened to the wrist by a wrist strap, within the housing the operating mechanism and the integrated electronics controllable by a plurality of electronic contacts and including at least one multi-celled display unit and a sensor unit with a plurality of sensors for various measurements are arranged, wherein at least one first microprocessor controls data processing, the display of values on the display unit and the saving of values, the operating mechanism comprising an effective connection with at least one operating element formed as a setting stem passing through the housing, the setting stem arranged within the operating mechanism in the housing and crossing the housing completely and in an active manner continuously through the housing and parallel to a planar enlargement of the housing, and moveably mounted rotatably about a rotational axis and linearly parallel to the rotational axis of the setting stem, a first watch button pin of the setting stem projecting out of the housing and connected to a first operating watch button for linearly and rotatable movement by a user fingertip for triggering the electronic contacts in a manner corresponding to movement directions of the setting stem, resulting in signals for controlling the electronics of the multifunctional device and the user capable of scrolling through menus and submenus.

2. The operating mechanism according to claim 1, wherein the setting stem (52) has a shaft part (52a) comprising the first watch button pin (527), a web (529), a first disc (520) and a second disc (521).

3. The operating mechanism according to claim 2, wherein the setting stem (52) interacts with a counter-contact part (52b) of the operating mechanism (5), the counter-contact part (52b) is rotatably moveable but linearly immovable and contacts at least one first rotational-direction contact (512) and at least one second rotational-direction contact (513).

4. The operating mechanism according to claim 1, wherein the setting stem (52) of the operating mechanism (5) has a neutral position wherein there is no deflection of the linear movement contact (510).

5. The operating mechanism according to claim 1, wherein the setting stem (52) of the operating mechanism (5) has a push position, in which the setting stem (52) is pushed from the side of the shaft part (52a) in a direction linearly parallel to the rotational axis of the setting stem (52) towards the housing (2) with the first operating watch button (56).

6. The operating mechanism according to claim 1, wherein the setting stem (52) of the operating mechanism (5) has a pull position in which the setting stem (52) is pulled away from the housing (2) from the side of the first operating watch button (56) in a direction linearly parallel to the rotational axis of the setting stem (52).

7. The operating mechanism according to claim 1, wherein a second operating watch button (57) is arranged diametrical to the first operating watch button (56), opposite the shaft part (52a), projecting out of the housing (2) and positively and/or non-positively releasably connected to a second watch button pin (528) of the setting stem (52).

8. The operating mechanism according to claim 7, wherein the setting stem (52) can be operated from both diametrically opposite sides of the housing (2).

9. The operating mechanism according to claim 7, wherein pushing the shaft part (52a) towards the housing (2) corresponds to pulling the setting stem (52) out of the housing (2) at the second operating watch button (57).

10. The operating mechanism according to claim 9, wherein the setting stem (52) is securable against an undesirable actuation by a locking lever (61), which is mounted with a profile disc (65) rotatably moveably mounted on the base plate (50).

11. The operating mechanism according to claim 7, wherein the first operating watch button (56) and/or the second operating watch button (57) has external teeth, so that the first operating watch button (56) and/or the second operating watch button (57) can be operated with wet hands or gloved hands.

12. The operating mechanism according to claim 11, wherein locking is achieved by pushing from a side of the shaft part (52a) towards the housing (2) or pulling the coupling part (52c) out of the housing (2) while simultaneously rotating the setting stem (52).

* * * * *